(12) United States Patent
Strubl et al.

(10) Patent No.: US 10,053,577 B2
(45) Date of Patent: Aug. 21, 2018

(54) POLYESTER AND POLYOLEFIN MOLDING COMPOSITIONS HAVING BIOACTIVE PROPERTIES AND MOLDINGS PRODUCED THEREFROM

(71) Applicant: Thueringisches Institut fuer Textil- und Kunststoff-Forschung e.V., Rudolstadt (DE)

(72) Inventors: Rüdiger Strubl, Saalfeld (DE); Klaus Heinemann, Rodolstadt (DE); Frank Schubert, Jena (DE); Ralf-Uwe Bauer, Rudoldstadt (DE); Sabine Riede, Uhlstadt-Kirchhasel (DE)

(73) Assignee: THUERINGISCHES INSTITUT FUER TEXTIL-UND KUNSTSTOFF-FORSCHUNG E.V., Rudolstadt (DE)

( * ) Notice: Subject to any disclaimer, the term of this patent is extended or adjusted under 35 U.S.C. 154(b) by 0 days.

(21) Appl. No.: 15/613,360

(22) Filed: Jun. 5, 2017

(65) Prior Publication Data
US 2017/0349745 A1  Dec. 7, 2017

(30) Foreign Application Priority Data
Jun. 6, 2016  (DE) .................. 10 2016 006 745

(51) Int. Cl.
| | |
|---|---|
| *C08G 63/02* | (2006.01) |
| *C08L 67/06* | (2006.01) |
| *C08K 3/00* | (2018.01) |
| *C08K 3/10* | (2018.01) |
| *C01G 9/04* | (2006.01) |
| *C08K 5/098* | (2006.01) |
| *C08F 220/26* | (2006.01) |
| *B29C 33/38* | (2006.01) |
| *B29C 45/00* | (2006.01) |
| *B29C 47/00* | (2006.01) |
| *C08K 3/015* | (2018.01) |
| *B29K 67/00* | (2006.01) |
| *C08K 3/16* | (2006.01) |

(52) U.S. Cl.
CPC .......... *C08L 67/06* (2013.01); *B29C 33/3807* (2013.01); *B29C 45/0001* (2013.01); *B29C 47/0004* (2013.01); *C01G 9/04* (2013.01); *C08F 220/26* (2013.01); *C08K 3/005* (2013.01); *C08K 3/015* (2018.01); *C08K 3/10* (2013.01); *C08K 5/098* (2013.01); *B29K 2067/003* (2013.01); *B29K 2067/006* (2013.01); *C08K 2003/168* (2013.01)

(58) Field of Classification Search
USPC ............................ 528/271, 272, 273, 274
See application file for complete search history.

(56) References Cited

FOREIGN PATENT DOCUMENTS

| | | |
|---|---|---|
| EP | 2 640 776 A2 | 9/2013 |
| JP | 2011-111704 | 6/2011 |

*Primary Examiner* — Terressa Boykin
(74) *Attorney, Agent, or Firm* — ProPat, L.L.C.

(57) ABSTRACT

The invention molecularly equips polyester or polyolefin molding compositions in situ with zinc ions before extrusion, enabling direct processing of the molding compositions from the melt even at high temperatures and ensuring a long-term antibacterial action. The inventive molding compositions include at least one polyester polymer or polyolefin polymer and at least one zinc salt-organoligand complex.

14 Claims, 3 Drawing Sheets

POLYESTER AND POLYOLEFIN MOLDING COMPOSITIONS HAVING BIOACTIVE PROPERTIES AND MOLDINGS PRODUCED THEREFROM

CROSS-REFERENCE TO RELATED APPLICATIONS

This application claims priority to German Patent Application 10 2016 006 745,4 filed Jun. 5, 2016, which is hereby incorporated herein by reference in its entirety.

FIELD OF THE INVENTION

The invention relates to polyester and polyolefin molding compositions moldable from the melt, in which through the use of specific complexed zinc salt compounds a long-term bioactive or biocidal, in particular antibacterial, action is obtained.

BACKGROUND OF THE INVENTION

Such sine salt organoligand complexes, in particular based on carboxylic acid-(2-oxazoline) derivatives are in principle known and have already been used for modification of the properties of polyamides (EP 2 640 776). However, it had to be noted that in contrast to polyamides with their typical, residual moisture concentrations of about (0.03-0.07) percent, the use of the zinc salt complexes described for modifying the properties of polyester and polyolefin molding compositions, on the one hand because of the relatively high zinc salt concentrations for obtaining antibacterial properties in comparison to the silver or silver ion concentrations known to those skilled in the art and their catalytic activity for polymer, in particular polyolefin, degradation reactions, and on the other hand because of their relatively high water content contained therein and the potential for hydrolysis associated therewith in the case of polyesters, was associated with very considerable difficulties, e.g. during use of the compounding and melt-spinning technology, as a consequence of dramatic polymer degradation processes and the complexes described therein were therefore not usable.

SUMMARY OF ADVANTAGEOUS EMBODIMENTS OF THE INVENTION

The objective of this invention thus consists in the provision of products produced by means of polymer melt molding methods, in particular moldings, which result from modified polyolefin and polyester melts, in which polymer additives are contained which are non-agglomerating, high temperature-resistant and incorporated by means of in-line technology, which are ionically bound zinc-based biocides and with which already with use of small quantities very good antibacterial properties are obtained with high permanence, high long-term activity, and surprising efficiency and combined therewith skin-care effects.

The known solutions have the disadvantage that high biocide contents have to be added, for example in the case of nanosliver or zinc oxide, since tor attainment of an appreciable bioactive action in the use for example of the fibers, the active species of the ionic forms of silver or zinc must first be formed in adequate concentrations. Further disadvantages are often agglomeration of the additives which seriously impair the processing of the polymers from melts into multifilaments just as do particles based on supported organic zeolites.

The invention solves the problem in that zinc salts are used with suitable complexing agents for zinc ions, so-called organoligands, which encapsulate zinc ions on a molecular basis and moreover ensure high thermodynamic compatibility both with polyolefin and also with polyester melts, are thermally stable at high processing temperatures and advantageously can be used directly in the processing procedures as masterbatch formulation, since only relatively small zinc ion concentrations are needed for efficient activity and it was possible to effect a so-called "in situ dewatering" in the production of these complexes, since in anhydrous media and with use of anhydrous zinc salts no such zinc ion-organo-ligand complexes based on 2-oxazoline derivatives of simple aliphatic or aromatic mono- and dicarboxylic acids are formed.

The complexed sine salt compounds consist of a combination of a zinc salt with a heterocyclic organic compound which acts as a ligand towards the metal cation and results in a stoichiometrically constituted, thermally stable complex compound. The complexed zinc salt compounds are present in molecular form, they can be processed directly with the polymer melt, they influence neither the viscosity of the melt nor the physical properties of the moldings, and in specific anhydrous formulations they exhibit no catalytic action on a possible polymer degradation, neither in polyesters nor in polyolefins. The zinc is present, directly in ionically stabilized form in the molding composition.

These molding compositions can be shaped by methods known to those skilled in the art for the production of moldings from polymer melts into various moldings, such as fibers, yarns, films, foams, plates and injection molded articles with permanent antibacterial properties.

The present invention thus has the following advantages:

simple synthesis of low water content active substances from inexpensive raw materials polymer additives universally suitable for processes for the melt processing of polyolefins and polyesters for example, but not exclusively, into fibers, films, injection molded articles, and various other moldings high thermal stability at temperatures of over 310° C.

thermodynamically compatible with polyolefins and polyesters no polymer degradation during processing and use no particle formation as a result of agglomerations in the polymer melts in-line use of the complexes in the processing process adaptation to existing processing technologies possible without process alterations normal handling, e.g. due to producibility and usability in the form of masterbatches low additive concentrations (<0.1%) suffice in order to obtain high biocidal, preferably antibacterial activities antibacterial action experimentally demonstrated in long-term trials and after 50 washes under industrial-conditions polyolefins and polyesters with these complexes as additives are biocompatible, display no cytotoxicity, i.e. they pass tests according to DIN EN ISO 10993-5, -4 and -10, and above ail have skin-care properties.

DETAILED DESCRIPTION OF ADVANTAGEOUS EMBODIMENTS OF THE INVENTION

In the industrial thermoplastics field, polyesters and polyolefins are among an important group of polymeric materials with predominantly hydrophobic properties. As an important construction material, polyester and polyolefin are mainly used as polyester and polyolefin fiber materials for textiles, nonwovens and microfibers, but are also processed into films or PET bottles.

The present invention relates to polyester and polyolefin compositions functionalized with zinc ions.

The antibacterial equipping of polyester and polyolefin molding compositions through the addition of zinc particles, mostly in the form of zinc oxide, is known. The disadvantage of zinc oxide particles consists in that here the particle size always plays an important part, and especially in the spinning of the molding compositions to fibers this must be restricted. In addition, the zinc must first be converted into an active ionic form, that is, the zinc oxide must first be dissolved and the moldings often tend to yellowing. These disadvantages can be overcome by using the zinc oxide particles only on the surface in coatings and in combination with titanium dioxide particles, as for example disclosed in JP 2011-111704.

This invention was therefore based on the problem of molecularly equipping the polyester and polyolefin molding compositions in situ with zinc ions before extrusion, enabling direct processing of the molding compositions from the melt even at high temperatures and ensuring a long-term antibacterial action. The otherwise usual additional process step of subsequent surface coating should be avoided, and zinc ions present in the interior of a molding should also be able to diffuse onto the surface and become active.

This problem is solved by means of polyester and polyolefin compositions molecularly equipped with zinc ions as claimed in claim 1.

The problem was solved by complexing zinc salts with carboxylic acid-(2-oxazoline) derivatives, which form thermodynamically very stable sine salt complexes. The organoligand complexes have the effect that the zinc is already stabilized in the active form as zinc ion by the ligands, is present as such molecularly in the molding composition, and homogeneously doped equipping with zinc ions becomes possible.

The problem described above is now solved in that at least one polyester polymer or polyolefin polymer and at least one zinc salt-organoligand complex is present in the polyester or polyolefin composition. The at least one polyester is preferably a polyethylene terephthalate (PET), a polybutylene terephthalate (PBT) or a polytrimethylene terephthalate (PTT). The at least one polyolefin is preferably a polyethylene or polypropylene.

For the functionalization of polyesters, in particular polyethylene terephthalate or polybutylene terephthalate, with zinc salt organoligand complexes, strict care must be taken that complexes are produced with exclusion of moisture and used in anhydrous formulation. This problem is solved in that during the production of the zinc salt organoligand complexes the water of crystallization is removed in situ.

According to the invention, as well as these polymers, copolyesters and copolyolefins, block copolyesters and block copolyolefins and polyester or polyolefin blends can also be used.

The complexed zinc salt compounds according to the invention are always built up of a combination of a zinc salt with an organoligand. The zinc salt can be any zinc salt which consists of a metal cation and an inorganic or organic anion. Examples of especially suitable zinc salts are zinc(II) chloride ($ZnCl_2$), zinc(II) iodide ($ZnI_2$), zinc sulfate ($ZnSO_4$) and zinc (II) acetate (Zn ($CH_3COO)_2$). The substances active as organoligand contained in the metal salt organoligand complexes are preferably 2-oxazoline derivatives of organic carboxylic acids. Unsubstituted 2-oxazolines (also described as 4,5-dihydrooxazoles) are heterocyclic 5-membered ring compounds which each contain an oxygen atom, a nitrogen atom and a double bond in the ring. The 2-oxazolines used according to the invention as organoligands contain the hetero atoms oxygen in the 1-position, the nitrogen in the 3-position and the double bond in the heterocyclic ring is located between carbon atom 2 and the nitrogen atom.

According to the invention, 2-oxazolines are used as derivatives of organic carboxylic acids. The organic carboxylic acid can be any carboxylic acid which is aliphatic, aromatic or aliphatic-aromatic in nature and is of monofunctional, bifunctional or polyfunctional structure as regards the number of carboxylic acid groups present.

Examples of suitable carboxylic acids from which 2-oxazoline derivatives according to the invention as ligand systems for the complexing of zinc cations contained in the zinc salts can be obtained are the monofunctional carboxylic acids palmitic acid [Chemical Abstracts Registration No. 57-10-3], stearic acid [CASRN 57-11-4], behenic acid [CASRN 112-85-6], lauric acid [CASRN 143-07-7], erucic acid [CASRN 112-86-7], and further the bifunctional carboxylic acids oxalic acid [CASRN 144-62-7], adipic acid [CASRN 124-04 -9], 2-bromoisophthalic acid [CASRN 2243-91-6], 4-bromoisophthalic acid [CASRN 6939-93-1], 5-bromoisophthalic acid [CASRN 23351-91-9], isophthalic acid [CASRN 121-91-5], terephthalic acid [CASRN 100-21-0], 2-bromoterephthalic acid [CASRN 586-35-6] and the trifunctional carboxylic acid trimesic acid [CASRN 554-95-0].

It was found that the monofunctional carboxylic acids in particular are suitable for the formation of the 2-oxazoline derivatives as a ligand system for the production of antibacterially equipped polyester and polyolefin fibers, while the bi- and trifunctional carboxylic acids lead to complications at the fine spinnerets and are therefore especially suitable for the production of polyester or polyolefin films and polyester or polyolefin injection molded items. Surprisingly, it was also found that 2-oxazoline derivatives formed with isophthalic acid [CASRN 121-91-5], terephthalic acid [CASRN 100-21-0] and 2-bromoterephthalic acid [CASRN 586-35-6] are very good for modifying the properties of polyamides, and considerably less suitable for the generation of antibacterial properties of polyesters and polyolefins.

Figure 1:
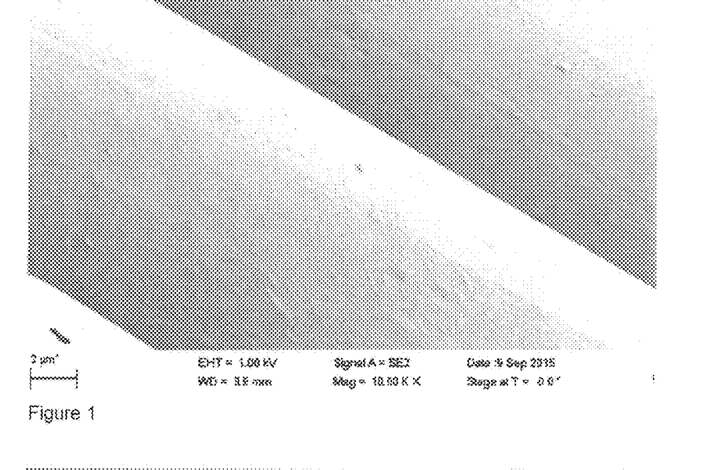
FIG. 1 is an SEM micrograph of a comparative PET fiber.
Figure 2:
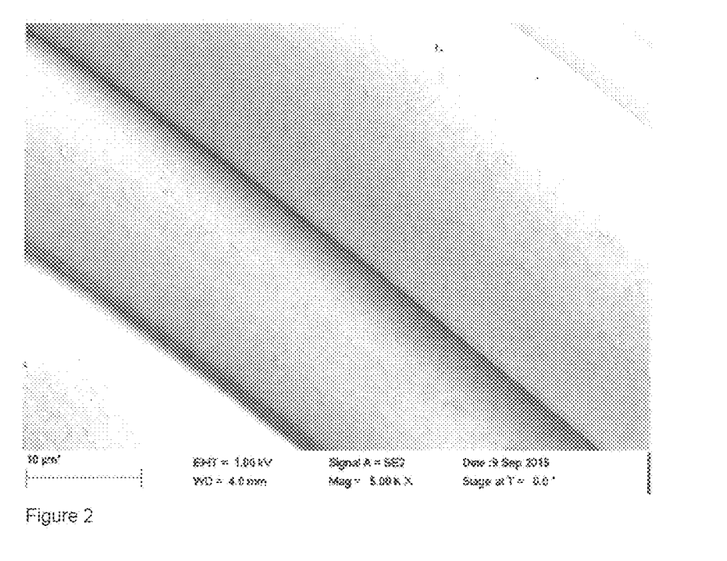
FIG. 2 is an SEM micrograph of an exemplary inventive PET fiber.

The zinc contents are homogeneously distributed in the polyester and polyolefin compositions according to the invention owing to their molecular form as organo-complex formulations. In the SEM micrographs FIG. 1 (PET fibers without zinc organoligand) and FIG. 2 (PET fibers with 0.2 mass % zinc iodide-behenic acid-2-oxazoline complex (corresponding to 250 ppm zinc in the polyester composition)), the sample surfaces of fibers are shown by way of comparison. It can clearly be discerned that the zinc contents of sample 2 have formed no larger agglomerations or particles on the fiber surface. This homogeneous zinc distribution, is caused in particular by the organophilic structure of the ligands in the organo-complexes.

The processing of the polymer molding compositions is in no way impaired, by the addition of the zinc salt-organoligand complex compounds. The polyester or polyolefin molding compositions with the added zinc complexes can be shaped from melts as usual by injection molding, deep-drawing, blow-molding or into monofils or filaments by melt-spin monofil or multifilament processing.

For the functionalization of polyolefin molding compositions, it has been found advantageous to use zinc salt-organoligand complex compounds with a high content of organic substance, which derives from the structure and the stoichiometry of the overall formulation of the organoligands used. This problems is solved in. that in the production of the zinc salt-organoligand complex compounds a stoichiometric ratio of organoligand to zinc compound of preferably 2 mol ligand: 1 mol zinc salt is maintained. Good processing properties, compatibilities and long-lasting effects are obtained when zinc salt-organoligand complex compounds are used in polyolefin molding compositions, in which an elemental carbon to zinc ratio of 4.5:1 to 10:1 (mol C: mol Zn), preferably 8:1 to 10:1, is maintained.

The modification of the polyester or polyolefin molding compositions with the complexed zinc salt compounds leads to no chemical changes in the molding compositions during the melt processing, if special conditions of moisture exclusion are observed in the processing of the zinc salt-organoligand complex compounds together with polyesters. The viscosities are not altered, and the zinc ions used show no catalytic action with regard to polymer degradation reactions. In addition, matting or increasing the degree of whiteness by addition of titanium dioxide is not necessary, the products remain pure white, and the dye affinity is not altered.

The universal processability of the zinc-containing molding-compositions from the melt into fiber products by normal melt spin technologies is found to be a particular embodiment of the invention. The antibacterial polyester and polyolefin molding compositions can be spun into continuous filaments (multifils), staple fibers or monofils and used to make various fiber products. Here it is possible to produce a fiber product completely from the zinc-containing fiber species or only with the aid of fractional incorporation of the same in mixtures with pure polymer fiber products. In this manner, various products with different antibacterial activity levels can be created.

As well as the textile applications, other use fields for plastic products of polyesters or polyolefins with permanent antibacterial properties are conceivable, for example door and grab handles, in plastics in the sanitary field, in plastics in the furniture industry, such as office or hospital furniture or also for the antibacterial equipping of medical engineering products. All these products are characterized by permanent antibacterial properties at only low concentrations of zinc ions, caused by the complexing of the zinc ions and the molecular distribution of the zinc ions.

Figure 3:
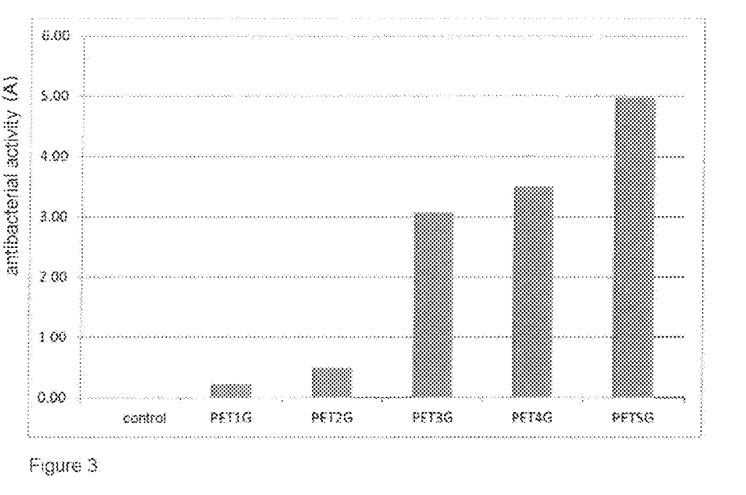
FIG. 3 graphically illustrates the adjustment of the antibacterial activities for inventive polyester fabrics.

The quantity of zinc which is incorporated in the form of the zinc salt-2-oxazoline complex compounds into the polyester or polyolefin molding compositions for effective antibacterial equipping is freely selectable over broad limits, as long as the mechanical properties of the molding compositions are not adversely affected. Through the organic encapsulation of the zinc salts by the organoligands, the zinc is provided directly in ionic form and molecularly. This has the advantage that the zinc doping lies markedly below the contents of often used particulate zinc oxides, and the zinc ions which lie in the interior of a molding can also become antibacterially active. Usually, the zinc content lies between 50 and 500 ppm based on the overall formulation depending on the antibacterial activity required. Excellent effects have even been demonstrated with zinc contents of 150 to 300 ppm zinc based on the overall formulation. In fibers, the preferred, concentration range of zinc contents lies between 100 and 250 ppm zinc (FIG. 3). Here it is immaterial whether the fiber was produced, as a multifil continuous filament, monofil, bicomponent fiber or staple fiber or a fabric thereof (Table 1, FIG. 3).

FIG. 3 shows possibilities for the adjustment of the antibacterial activities of polyester fabrics via the concentration, of the zinc contents in the processed fibers.

TABLE 1

Antibacterial activity of PET fabrics with various zinc contents, testing according to DIN 20743; A > 2: significant action; A > 3: strong action

| Fabric sample | Zinc (ppm) | $c_8$ [CFU/ml] 0 h | $c_8$ [CFU/ml] 24 h | $IgC_8$ 0 h | $IgC_8$ 24 h | F $\log_{24\,h} - \log_{0\,h}$ | G $\log_{24\,h} - \log_{0\,h}$ | A (F-G) | S.D. |
|---|---|---|---|---|---|---|---|---|---|
| Control | 0 | 437E+04 | 6.61E+07 | 4.6 | 7.8 | 3.18 | — | 0.00 | 0.08 |
| PET1G | 0 | — | 3.93E+07 | — | 7.6 | — | 2.96 | 0.22 | 0.06 |
| PET2G | 63 | — | 2.09E+07 | — | 7.3 | — | 2.68 | 0.50 | 0.08 |

TABLE 1-continued

Antibacterial activity of PET fabrics with various zinc contents, testing according to DIN 20743; A > 2: significant action; A > 3: strong action

| Fabric sample | Zinc (ppm) | $c_8$ [CFU/ml] 0 h | $c_8$ [CFU/ml] 24 h | $lgC_8$ 0 h | $lgC_8$ 24 h | F $log_{24 h}$ - $log_{0 h}$ | G $log_{24 h}$ - $log_{0 h}$ | A (F-G) | S.D. |
|---|---|---|---|---|---|---|---|---|---|
| PET3G | 129 | — | 6.27E+05 | — | 4.7 | — | 0.11 | 3.07 | 2.12 |
| PET4G | 276 | — | 1.41E+05 | — | 4.3 | — | -0.32 | 3.50 | 1.74 |
| PET5G | 385 | — | 9.33E+02 | — | 2.8 | — | -1.79 | 4.97 | 0.47 |

Figure 4:
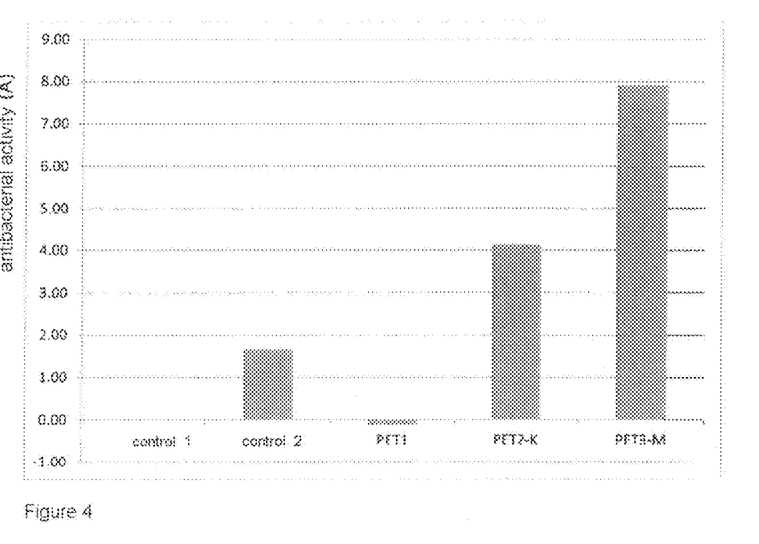
FIG. 4 graphically illustrates the antibacterial activity of exemplary inventive bi-component polyester and polyolefin fibers.

A further embodiment according to the invention is the possibility of being able to distribute the zinc-containing fractions in a fiber with predetermined fractions in a specific and geometrically defined manner over the fiber cross-section. For this, a special bi-component spinning-technology is used, in which a zinc-containing and a zinc-free polymer molding composition respectively are simultaneously fed into a bi-component spinneret and a fiber product is drawn out from this. Various bi-component fibers can be produced, for example with "core-sheath" structure, or of the "side-by-side", "isle in the sea" or "segmented pie" type. If a zinc-containing polyester or polyolefin molding composition is used in a spinning process for the production of fibrous products with a core-sheath structure, then by feeding the zinc products with the sheath polymer for example fibers are obtained in which zinc domains are concentrated on the fiber surface, which in later use rapidly lead to spontaneous and effective antibacterial functionality. If on the other hand a zinc-containing polymer molding composition is fed into the core polymer of the bi-component fiber, the antibacterial action is delayed and advantageously has a permanent long-term action with depot function. This effect can be explained very well on core/sheath fibers thus produced which were produced, with equal zinc concentration in either. It was observed that in core/sheath fibers in which the zinc doping was effected in the polymer molding composition of the sheath, a quite large quantity of zinc ions very rapidly becomes active and the antibacterial action thus turns out higher than in fibers in which the zinc doping was performed only in the polyester or polyolefin molding composition of the core. The zinc ions from the core fibers also become active, and can thus migrate to the fiber surface of the sheath. At the same time, the action of the sine ions from the core fiber as regards the antibacterial equipping is retarded and takes place over a longer period. In this manner, through the deliberately introduced distribution structure of the zinc contents into a polymer molding composition, various activity levels can be set for the antibacterial equipping, and targeted on the use of the molding compositions, as can be shown in the example of core-sheath fibers. FIG. 4 shows the graded setting of the antibacterial activity of bi-component polyester and polyolefin fibers with core-sheath structure by distribution of the zinc contents in the core (PET2-K) or sheath (PET3-M) of the fibers.

TABLE 2

Antibacterial activity of PET bi-component fibers of the core/sheath type with equal zinc contents in the core (PET2-K) and sheath (PET3-M) respectively, testing according to DIN 20743; A > 3.3: significant action; A > 7.9: biocidal action

| Bi-co-fiber | Zinc (ppm) | $c_8$ [CFU/ml] 0 h | $c_8$ [CFU/ml] 24 h | $lgC_8$ 0 h | $lgC_8$ 24 h | F $log_{24 h}$ - $log_{0 h}$ | G $log_{24 h}$ - $log_{0 h}$ | A (F-G) | S.D. |
|---|---|---|---|---|---|---|---|---|---|
| Contr. 1 | 0 | 5.20E+04 | 8.20E+07 | 4.7 | 7.91 | 3.25 | 3.25 | 0.00 | 0.10 |
| Contr. 2 | Genta. | | 2.40E+06 | | 6.2 | | 1.59 | 1.67 | 0.42 |
| PET1 | 0 | — | 1.10E+08 | — | 8.03 | — | 3.38 | -0.13 | 0.09 |
| PET2-K | 340 | — | 7.80E+03 | — | 3.77 | — | -0.88 | 4.14 | 0.43 |
| PET3-M | 340 | — | 0.00E+00 | — | 0.00 | — | -4.65 | 7.91 | 0.00 |

Figure 5:
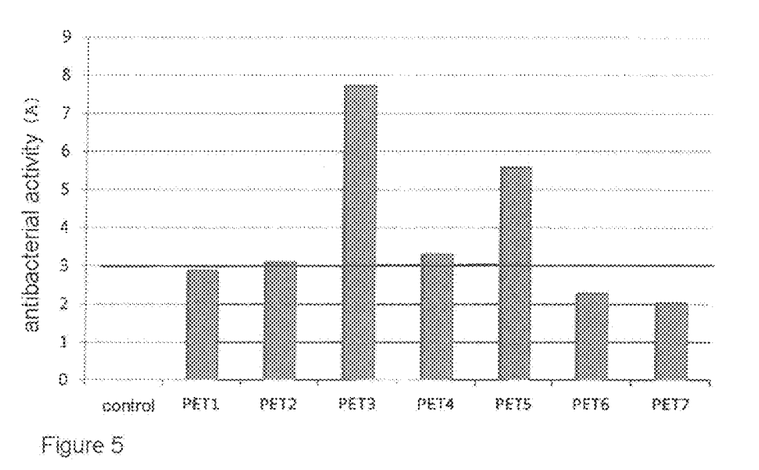
FIG. 5 graphically illustrates the antibacterial activity of various exemplary inventive fibers

Furthermore, the polyester and polyolefin compositions according to the invention are outstandingly suitable with regard to the adjustment of further additional material properties. This variable modification possibility of polyester and polyolefin molding compositions is obtained in particular due to the fact that various zinc salts with different anions form stable metal salt-organoligand complex compounds. As a result, very advantageously the effective zinc contents usually incorporated into molding compositions can be obtained by processing different zinc salt complex compounds, depending on which zinc salt was used with which organoligand for the complex formation. In this way, it is simple to implement that possibly undesired anions in the molding composition can be avoided or the antibacterial activity of the molding compositions can be weakened or intensified, see Table 3, FIG. 5. Thus by simple choice of the zinc compound, an antibacterial activity spectrum between bacteriostatic to biocidal can already be set in the production process of shaping of the molding compositions. Other anti-bacterially active metal salts such as the salts of silver or copper A can also be complexed by appropriate organoligands and used singly or in mixtures with zinc and can thus contribute to the intensification of the action.

TABLE 3

Antibacterial activity of PET fibers with various zinc additives and concentrations, testing according to DIN 20743; A > 2: significant action; A >23: strong action

| Fiber Sample | Zinc salt | Zn (ppm) | $c_8$ [CFU/ml] 0 h | $c_8$ [CFU/ml] 24 h | $lgC_8$ 0 h | $lgC_8$ 24 h | F $log_{24\,h^-}$ $log_{0\,h}$ | G $log_{24\,h^-}$ $log_{0\,h}$ | A (F-G) | S.D. $W_A$ |
|---|---|---|---|---|---|---|---|---|---|---|
| Control | — | 0 | 5.53E+04 | 5.40E+07 | 4.74 | 7.73 | 2.99 | 2.99 | 0.00 | 0.06 |
| PET 1 | — | 0 | | 7.50E+04 | — | 4.85 | — | 0.11 | 0.88 | 0.17 |
| PET 2 | ZnI2 | 50 | | 5.10E+04 | — | 4.63 | — | −0.11 | 3.10 | 0.35 |
| PET 3 | ZnI2 | 100 | | 0.00E+00 | — | 0.00 | — | −4.74 | 7.73 | 0.00 |
| PET 4 | ZnSO4 | 50 | | 4.80E+04 | — | 4.42 | — | −0.32 | 3.31 | 0.58 |
| PET 5 | ZnSO4 | 100 | | 3.00E+03 | — | 2.14 | — | −2.60 | 5.59 | 1.99 |
| PET 6 | Zn(Ac)2 | 50 | | 3.00E+05 | — | 5.44 | — | 0.70 | 2.29 | 0.26 |
| PET 7 | Zn(Ac)2 | 100 | 7.50E+04 | 5.00E+04 | — | 5.69 | — | 0.95 | 2.04 | 0.11 |

The zinc contents introduced into the polymer molding compositions by means of the complexed zinc salt compounds according to the invention are resistant to extraction and emission. In single-component polyester or polyolefin fibers which had been doped with different complexed zinc salt compounds, almost the originally introduced zinc content could be detected even after up to 50 standardized, washing procedures (Table 4). In addition, good antibacterial activity was still detected after these washing processes.

TABLE 4

Stability of the zinc doping towards aqueous extraction (washing method for fibers according to DIN EN ISO 105-C08/C09: 2003)

| Multifil fiber | Zinc salt used in the complex | Zinc content (ppm) in the fiber Initial value | After 25 washes | After 50 washes |
|---|---|---|---|---|
| PET 1 | $ZnI_2$ | 63 ± 6 | 57 ± 6 | 54 ± 6 |
| PET 2 | $ZnSO_4$ | 24 ± 3 | 19 ± 2 | 19 ± 2 |
| PET 3 | $ZnI_2$ | 18 ± 2 | 14 ± 2 | 14 ± 2 |
| PET 4 | $ZnI_2$ | 126 ± 12 | 121 ± 12 | 122 ± 12 |

The fiber products resulting from the melt processing of the polyester or polyolefin compositions according to the invention into filaments, monofils or staple fibers are biocompatible. Specific tests according to DIN 10993-1 to 10 have shown that no sensitization reactions derive from the fibers, these have no hemolytic potential and also have no cytotoxic properties.

The polyester- or polyolefin compositions according to the invention can without restrictions be provided and processed with other usual additives, fillers, processing aids, color pigments or lubricants, without the functionalization effect being impaired. Because of the advantages described, the polyester or polyolefin compositions are particularly suitable for the production of moldings and structural parts, plates and films. Use fields here in particular in the medical engineering field and tor the packaging of foods are possible. The production of functionalized fibers or filaments is also very possible. The applications here especially lie in the field of industrial textiles or antibacterially equipped textile fibers for clothing with odor-inhibiting properties or for medical applications or also in the hygiene products field.

The production of the polymer compositions is usually effected by mixing at least one polyester or polyolefin with at least one metal salt-organoligand complex. The mixing of the components can be effected in normal mixing devices.

For this, polyester or polyolefin in chip form, small plate form or as granules is premixed with an organo-complex in powder form, and the mixture melted together in a suitable apparatus and homogenized in the melt by the action of shear forces. Preferably, however, the procedure used is such that a premix of a metal salt-organoligand metal complex is produced in the form of a masterbatches or preconcentrate and this is later mixed with the pure polyester and polyolefin in the production of the semi-finished or end product, optionally by means of side-stream metering on an extrusion machine. The content of the metal salt organoligand complex in a masterbatch is determined by the compatibility with the matrix material, the intended degree of functionalization and the desired final concentration in the compound. It is possible to produce preconcentrates up to a concentration of 20 mass percent of metal salt-organoligand complex. A preferred metal ion concentration in a universally usable masterbatch formulation is 10,000 ppm zinc content.

If zinc ion-containing metal salt-organoligand complex compounds are produced for the production of active substance concentrates in the form of masterbatches with zinc ion concentrations of for example 10,000 ppm zinc (corresponds to 1 mass percent zinc) for the functionalization of polyesters, strict care must be taken that anhydrous zinc salt-organoligand complex compounds are used in the extrusion process. Polyethylene terephthalate or polybutylene terephthalate can usually only be spun into fibers without polymer degradation with residual moisture contents of less than 0.001 mass % moisture (10 ppm). It was found that for example the zinc-organoligand complex compound which was produced by use of zinc sulfate heptahydrate and processed with polybutylene terephthalate into a masterbatch by melt extrusion leads to considerable polymer degradation processes. This can be attributed to the stored water of crystallization, which in the zinc salt, heptahydrate is present at a content of 37 mass percent in its salt and on admixture of 14 mass percent to obtain a zinc ion concentration of 10,000 ppm introduces ca. 500 ppm moisture into the molding composition, which finally causes the considerable degradation of the polyester matrix. If on the other hand anhydrous zinc sulfate or the monohydrate is used for formulating the zinc salt-organoligand complex compound, the problem of the hydrolytic polymer degradation in the extrusion process does not occur. The experimental test data are shown in Table 5.

TABLE 5

Comparison of the intrinsic viscosity of PET masterbatches after formulation with a zinc salt-organoligand complex consisting of lauric acid-organoligand zinc sulfate heptahydrate (PET 2) and zinc sulfate monohydrate (PET 3) respectively in comparison to the polyester matrix with no addition (PET)

| Masterbatch 10,000 ppm zinc | Zinc salt used in the complex | Zinc content masterbatch (ppm) | Intrinsic viscosity (IV) $1^{st}$ value | $2^{nd}$ value |
|---|---|---|---|---|
| PET | without | 0 | 0.63 | 0.62 |
| PET 2 | ZnSO$_4$ × 7 H$_2$O | 9887 ± 100 | 0.41 | 0.38 |
| PET 3 | ZnSO$_4$ × 1 H$_2$O | 9946 ± 100 | 0.60 | 0.61 |

The masterbatch PET 2 functionalized with the zinc sulfate heptahydrate showed considerable polymer degradation, and the material cannot be stably used for the production of polyester multifilaments.

The problem was now solved in that for the synthesis of the zinc salt-organoligand complex compound based, on sine sulfate the heptahydrate is dewatered in situ in ethanolic solution and in this manner converted into its monohydrate and in this form used for the formation of the zinc sulfate organo ligand complex, and no longer causes additional polymer damage PET 3).

The bioactive in situ or biocidal in situ, above all antibacterial in situ functionalized polyester or polyolefin compositions according to this invention and the functionalized moldings and products produced therefrom in known processes consist of aromatic and/or aliphatic polyesters or polyolefins. Inter alia, but not restricted thereto, they contain polyethylene terephthalate (PET), polytrimethylene terephthalate (PTT), polybutylene terephthalate (PBT), poly-glycolides (PGA), polylactides (PLA), polyhydroxyalkanoates (PHA, PHB), aromatic and/or aliphatic polyester and polyolefin copolymers and polyester and polyolefin and copolyester and polyolefin mixtures and/or thermoplastic elastomers, inter alia, but not limited thereto, those on an ester basis. In addition, thermoset polyester molding compositions can be thus functionalized according to the invention. As a result of a processing and production process corresponding to the prior art, monofilaments, multifilaments and/or fibers, also flock fibers and products therefrom, based on this, but not limited thereto, are formed. Films, injection-molded parts and other products based thereon can be produced or the bioactive in situ or biocidal in situ, above all antibacterial in situ functionalized polymer compositions according to the invention find use in corresponding known applications. All products and derived products thus industrially produced or industrially utilized applications are each characterized by inherently long-lasting persistence and inherently high efficiency of the resulting bioactive or biocidal, above all antibacterial activity. The bioactive efficacy can be adjusted through the concentration of the zinc ions in the polymer composition and through the design of the molding. Thus the mode of action, the release rate and the duration of the action can be adjusted through the level of the doping of the polymer molding compositions with the zinc ions and with fibers and filaments through the production of bicomponent fibers. Thus for example with core/sheath fibers an antibacterial action of the zinc could always foe detected, irrespective of whether the zinc salt-2-oxazoline complex was located in the sheath or in the core of the bicomponent fiber. If the doping is effected in the sheath, the active substance release takes place faster and at higher levels, and with doping of the core, the active substance release becomes slower, but over a longer period.

In addition, the products obtained with use of bioactive in situ or biocidal in situ, above all antibacterial in situ functionalized polyester and polyolefin compositions produced according to the invention and the corresponding applications are characterized by extraordinary environmental and skin compatibility and by extremely low cytotoxicity and the inherent biological activity, above all the inherent antibacterial action continues long-term, since microorganisms of all kinds develop no resistances.

EXAMPLE 1

Laurie Acid-(2-Oxazoline)-Zn(II) Sulfate Complex (Zn(II)-12S)

The organoligand was produced from lauric acid via an esterification step with subsequent aminolysis with ethanolamine and thereafter a dehydrating ring closure reaction under the action of catalysts in the following manner:

100 g of lauric acid were mixed with 600 ml methanol and 20 ml conc. hydrochloric acid and boiled for 3 hrs under reflux. Most of the methanol was distilled off, and the organic phase was separated after cooling. The crude ester was washed with ice-water three times, dried and fractionated under vacuum. The product, was collected at 100 to 120° C. under a vacuum of 0.1 mbar.

Yield: 94%, liquid Sap. No.: 262.5 (th. 261.7)

The lauric acid-(2-oxazoline)-Sn(II) sulfate complex was obtained in a stirred apparatus, by firstly dissolving 10 g of zinc sulfate heptahydrate containing water of hydration in 30 ml dried ethanol and keeping this mixture gently boiling for 10 minutes. In this way, the heptahydrate was dehydrated by ligand exchange, whereby the monohydrate was formed. The dehydration process could be monitored by withdrawing the liquid phase from the ethanolic mixture and testing for the presence of dehydration, water after addition of white copper sulfate. If a blue coloration is no longer observed, zinc sulfate monohydrate is present. This was filtered off at the pump arid dried at 75° C.

For the complex formation, 2.85 g of zinc sulfate monohydrate were placed in dried ethanol and a solution of 5.0 g of lauric acid ligand in 50 ml dry ethanol was added dropwise to this. With stirring, a white precipitate formed and the mixture was then stirred for a further 2 days at room temperature. The complex was obtained by filtration at the pump and drying.

Yield: 5-6 g

| Elemental analysis: | C | H | N | Zn |
|---|---|---|---|---|
| theor.: | 54.9 | 8.9 | 4.6 | 10.7 |
| found: | 52.9 | 8.6 | 4.0 | 11.0 |

Ligand ratio: 2:1
Carbon-zinc ratio: 4.8:1

The following example was particularly suitable for the functionalization of polyolefins.

EXAMPLE 2

Behenic Acid-(2-Oxazoline)-Zn (II) Acetate Complex (Zn (II) -22Ac)

The organoligand from behenic acid was prepared analogously to example 1, by mixing 100 g of behenic acid with 800 ml methanol and 45 ml conc. HCl and keeping under reflux, under N$_2$ for 3 hours, and the mixture was then transferred still hot into a beaker and cooled slowly with stirring. During this, the crude ester was obtained in granulated form. It was filtered off, added to 150 ml water and this mixture neutralized with 5% $K_2CO_3$ solution. The solid product was filtered off again at the pump and recrystallized from 200 ml acetone. The ester crystallized overnight in the refrigerator as a fine precipitate, it was filtered, off at the pump and dried under vacuum at 40° C.

Yield; 36% M.Pt.: 52-54° C.

Saponification number; 154.7

The organoligand was prepared by slowly heating 142 g of methyl behenate, 61 g of ethanolamine and 1.4 g of titanium(IV) butylate to 140-175° C. under an $N_2$ atmosphere and methanol was distilled off in the process. After this, excess ethanolamine was removed under reduced pressure, firstly at ca. 400 mbar, then at 20 mbar, until the temperature in the condenser decreased. Next, the crude oxazoline was distilled under vacuum. Under a vacuum of 0.038 mbar, the product was taken off between 205 and 245° C. head temperature.

Yield: 105 g (48%) M.Pt.; 57° C.

Purity: 85-92%

The zinc acetate-organoligand complex was obtained by reacting the organoligand from behenic acid with zinc(II) acetate. In a stirred, apparatus, firstly 10 g of zinc (II) acetate dihydrate containing water of hydration was dissolved in 30 ml dried ethanol. This mixture was kept gently boiling for 7 minutes. During this, the dihydrate was dehydrated by ligand exchange and the monohydrate was formed. The dehydration process could be monitored by withdrawing the liquid phase from the ethanolic mixture and testing for the presence of dehydration water after addition of white copper sulfate. If a blue color is no longer observed, zinc sulfate monohydrate is present. This was filtered off at the pump and dried at 75° C.

For the complex formation, 1.8 g of zinc(II) acetate monohydrate were placed in dried, ethanol, and a solution of 7.3 g of organoligand from behenic acid in 100 ml dry ethanol was added dropwise to it. The mixture was further stirred and after 2 days the complex was obtained as a precipitate, which was then filtered off at the pump and dried.

Yield: 4-5 g

| Elemental analysis: | C | H | N | Zn |
|---|---|---|---|---|
| theor.: | 68.3 | 11.0 | 3.0 | 7.1 |
| found: | 68.1 | 11.3 | 3.0 | 6.4 |

Ligand ratio: 2:1
Carbon-zinc ratio: 9.7:1

EXAMPLE 3

In a Haake RHEOMEX® PTW16/25 p double screw extruder with a revolution rate of 120 $min^{-1}$, a masterbatch was produced at 270° C. from the homopolymer polyester 4048 from Invista and the zinc salt-organoligand. oxazoline complex.

Variant A—zinc iodide-lauric acid complex with 1250 ppm Zn

Variant B—zinc sulfate-behenic acid complex with 1000 ppm Zn

Variant C—zinc acetate-behenic acid complex with 1000 ppm Zn

EXAMPLE 4

In the melt spinner, the PET 4048 was mixed without additives as comparison sample (PET1) or the respective masterbatch was mixed with the polyester granules 4048, so that spin melts with the following compositions were formed:

PET2—Masterbatch A, 50 ppm $Zn^{2+}$
PET3—Masterbatch A, 100 ppm $Zn^{2+}$
PET4—Masterbatch B, 50 ppm $Zn^{2+}$
PET5—Masterbatch B, 100 ppm $Zn^{2+}$
PET6—Masterbatch C, 50 ppm $Zn^{2+}$
PET7—Masterbatch C, 100 ppm $Zn^{2+}$ The melts were spun via spinneret packs with a 24-hole spinneret into fibers of fineness 250 dtex and stored on spools.

EXAMPLE 5

The threads from the spinner spools were stretched with a stretch ratio of 1:3 to give a POY smooth yarn and the thread parameters determined (see Table 3a).

TABLE 6

Comparison of the thread parameters

| Sample | Fineness dtex | Tensile elongation % | Tensile strength cN/tex | E modulus MPa |
|---|---|---|---|---|
| PET1 | 81 | 28 | 45 | 11287 |
| PET2 | 83 | 40 | 40 | 11050 |
| PET3 | 83 | 41 | 38 | 10855 |
| PET4 | 85 | 40 | 36 | 10364 |
| PET5 | 84 | 38 | 34 | 9998 |
| PET6 | 82 | 33 | 37 | 10594 |
| PET7 | 83 | 42 | 36 | 10200 |

It is found that the tensile elongation in comparison to the comparison sample was increased in all samples and increases up to 150% of the comparison sample. Tensile strength and E modulus reduce in all samples, and in sample 5 the tensile strength sank to 76% of the comparison sample value and the E modulus to 89%.

EXAMPLE 6

The fibers produced in experiments 8 to 10 were tested with regard to their antibacterial activity, see results in Table 3. It was found that the zinc iodide-lauric acid complexes with 100 ppm $Zn^{2+}$ showed the strongest antibacterial action, followed by the zinc sulfate-behenic acid complexes with 100 ppm $Zn^{2+}$. The zinc iodide-lauric acid and zinc sulfate-behenic acid complexes with $Zn^{2+}$ contents of 50 ppm also still showed a very strong antibacterial action. The zinc acetate-behenic acid complexes at both zinc ion concentrations still showed significant antibacterial action.

That which is claimed:

1. Polyester or polyolefin polymer compositions comprising polyester or polyolefin doped with zinc salt-2-oxazoline complexes and thereby bioactively functionalized,
   wherein the zinc is present in ionic form and the zinc ions are molecularly distributed in the polymer composition, and the sine ions are present at a content, in a range from 20 ppm to 10,000 ppm, based on a total weight, of the composition.

2. The composition as claimed in claim 1, wherein the content of zinc ions lies in the range from 50 to 500 ppm, based on the total weight of the composition.

3. The composition as claimed in claim 2, wherein the content of zinc ions lies in the range from 250 to 350 ppm, based on the total weight of the composition.

4. The composition as claimed in claim 1, wherein the zinc ions are contained in zinc salt, complex compounds, and the zinc salt is zinc iodide, zinc chloride, zinc acetate or zinc sulfate.

5. The composition as claimed, in claim 4, wherein the complex compound comprises a 2-oxazoline derivative of aliphatic or aromatic carboxylic acids or dicarboxylic acids.

6. The composition as claimed in claim 5, wherein the 2-oxazoline derivatives are derivatives of palmitic acid, stearic acid, behenic acid, lauric acid, erucic acid, oxalic acid, adipic acid, 2-bromo-isophthalic acid, 4-bromoisophthalic acid, 5-bromo-isophthalic acid, isophthalic acid, terephthalic acid, 2-bromoterephthalic acid or trimesic acid.

7. The composition as claimed in claim 1, wherein the polyester is an aromatic and/or aliphatic polyester.

8. The composition as claimed in claim 7, wherein the polyester is a polyethylene terephthalate (PET), polytrimethylene terephthalate (PTT) or polybutylene terephthalate (PBT), a polyglycolide (PGA), a polylactide (PLA), a polyhydroxyalkanoate (PHA, PHB) an aromatic and/or aliphatic polyester copolymer or a mixture of polyesters and copolyesters, an ester-based thermoplastic elastomer and/or a thermosetting polyester molding composition.

9. A molding in the form of monofilaments, multi-filaments and/or fibers, flock fibers, multicomponent fibers, films or injection molded, parts comprising the bioactive functionalized polymer composition as claimed in claim 1, wherein said molding has permanent antibacterial properties.

10. The molding as claimed in claim 9, wherein, the bioactive action is long-lasting and after 50 washings at least 90% of the zinc ions are still present and active.

11. The molding as claimed in claim 9, wherein said molding is structured as a core/sheath fiber and the zinc ion-containing polyester or polyolefin composition is contained either in the sheath polymer or in the core polymer or in different concentrations in the core and sheath polymers.

12. The molding as claimed in claim 9, wherein the molding is bioactive and the zinc ion concentration in the molding lies between 50-500 ppm.

13. A method for producing the molding as claimed in claim 9, comprising
   mixing anhydrous polyesters or polyolefins with anhydrous zinc salt organoligand complexes, wherein water of crystallization is removed from the complexes in situ,
   converting the mixture into a melt and
   shaping the melt into a molding.

14. The method as claimed in claim 13, wherein the shaping comprises extruding or injection molding.

* * * * *

UNITED STATES PATENT AND TRADEMARK OFFICE
CERTIFICATE OF CORRECTION

PATENT NO. : 10,053,577 B2
APPLICATION NO. : 15/613360
DATED : August 21, 2018
INVENTOR(S) : Strubl et al.

Page 1 of 1

It is certified that error appears in the above-identified patent and that said Letters Patent is hereby corrected as shown below:

In the Claims

Column 14
Claim 1, Line 62, delete "sine" insert --zinc--
Claim 1, Line 63, delete "weight," insert --weight--

Column 16
Claim 9, Line 3, delete "molded," insert --molded--

Signed and Sealed this
Twenty-third Day of October, 2018

Andrei Iancu
*Director of the United States Patent and Trademark Office*